(12) United States Patent
Epstein

(10) Patent No.: US 6,486,380 B1
(45) Date of Patent: Nov. 26, 2002

(54) PANCREATIC β CELL HEXOKINASE TRANSGENE

(75) Inventor: Paul N. Epstein, Grand Forks, ND (US)

(73) Assignee: University of North Dakota Medical Education Research Foundation, Grand Forks, ND (US)

( * ) Notice: Subject to any disclaimer, the term of this patent is extended or adjusted under 35 U.S.C. 154(b) by 0 days.

(21) Appl. No.: 08/169,613

(22) Filed: Dec. 17, 1993

(51) Int. Cl.$^7$ ............ A01K 67/027; A01K 67/00; C12N 15/63; C07H 21/04

(52) U.S. Cl. ............ 800/18; 800/8; 800/9; 536/23.1; 435/320.1; 435/455

(58) Field of Search ............ 514/44; 800/2, 800/18, 9; 536/23.1, 24.1, 23.2, 23.5; 435/172.3, 69.1, 455, 320.1

(56) References Cited

PUBLICATIONS

Epstein Et Al. 1992. Proc. Natl Acad Sci, USA 89:12038–12042.*
Ward Et Al. 1991. Experientia 47:913–921.*
Van Brunt, 1988. Biotechnology 6(10):1149–1154.*
Wilmut Et Al., Jul. 7, 1998. New Scientist p. 56–59.*
Epstein, P.N. (1992) Analysis of Insulin Secretion Mechanisms Using Transgenic Mice. In: Transgenic Animal Models in Biomedical Research. (D.C. Scarpelli and G. Migaki, eds.) Academic Press, pp. 39–42.
Voss–McCowan, M.E., A Yeast Hexokinase Transgene Decreases Pancreatic Insulin and Transiently Reduces Diabetes, 1993, Transgene, Vo. 1, pp. 103–111.
Epstein, Paul N., Expression of Yeast Hexokinase in Pancreatic β Cells of Transgenic Mice Reduces Blood Glucose, Enhances Insulin Secretion, and Decreases Diabetes, 1992, Proc. Natl. Acad. Sci. USA vol. 89, pp. 12038–12042.

* cited by examiner

*Primary Examiner*—R Shukla
(74) *Attorney, Agent, or Firm*—McKee, Voorhees & Sease, P.L.C.

(57) ABSTRACT

A transgenic animal containing germ cells and somatic cells which contain a non-native recombinant gene which codes upon expression hexokinase capable of expressing hexokinase at significantly increased levels for study of the role of hexokinase in diabetes and other diseases. When these transgenic animals were exposed to a calmodulin stimulated model of diabetes increased levels of hexokinase activity were able to promote insulin secretion thereby reducing glucose levels in blood and transiently reduce the effects of diabetes.

2 Claims, 7 Drawing Sheets

```
GATCCCCCAA CCACTCCAAG TGGAGGCTGA GAAAGGTTTT GTAGCTGGGT AGAGTATGTA      60

CTAAGAGATG GAGACAGCTG GCTCTGAGCT CTGAAGCAAG CACCTCTTAT GGAGAGTTGC     120

TGACCTTCAG GTGCAAATCT AAGATACTAC AGGAGAATAC ACCATGGGCT TCAGCCCAGT     180

TGACTCCCGA GTGGGCTATG GGTTTGTGGA AGGAGAGATA GAAGAGAAGG GACCTTTCTT     240

CTTGAATTCT GCTTTCCTTC TACCTCTGAG GGTGAGCTGG GGTCTCAGCT GAGGTGAGGA     300

CACAGCTATC AGTGGGAACT GTGAAACAAC AGTTCAAGGG ACAAAGTTAC TAGGTCCCCC     360

AACAACTGCA GCCTCCTGGG GAATGATGTG GAAAAATGCT CAGCCAAGGA CAAAGAAGGC     420

CTCACCCTCT CTGAGACAAT GTCCCCTGCT GTGAACTGGT TCATCAGGCC ACCCAGGAGC     480

CCCTCTTAAG ACTCTAATTA CCCTAAGGCT AAGTAGAGGT GTTGTTGTCC AATGAGCACT     540

TTCTGCAGAC CTAGCACCAG GCAAGTGTTT GGAAACTGCA GCTTCAGCCC CTCTGGCCAT     600

CTGCTGATCC ACCCTTAATG GGACAAACAG CAAAGTCCAG GGGTCAGGGG GGGGGTGCTT     660

TGGACTATAA AGCTAGTGGG GATTCAGTAA CCCCCAGCCC TAAGTGACCA AGCTATTTTT     720

TCGCTTTTTC TTTGAAAAGG TTGTAGGAAT ATAATTCTCC ACACATAATA AGTACGCTAA     780
```

```
TTAAATAAA ATG GTT CAT TTA GGT CCA AAA AAA CCA CAA GCC AGA AAG          828
          Met Val His Leu Gly Pro Lys Lys Pro Gln Ala Arg Lys
            1               5                   10

GGT TCC ATG GCC GAT GTG CCA AAG GAA TTG ATG CAA CAA ATT GAG ATT        876
Gly Ser Met Ala Asp Val Pro Lys Glu Leu Met Gln Gln Ile Glu Ile
        15               20                  25

TTT GAA AAA ATT TTC ACT GTT CCA ACT GAA ACT TTA CAA GCC GTT ACC        924
Phe Glu Lys Ile Phe Thr Val Pro Thr Glu Thr Leu Gln Ala Val Thr
30                  35                  40                  45

AAG CAC TTC ATT TCC GAA TTG GAA AAG GGT TTG TCC AAG AAA GGT GTT        972
Lys His Phe Ile Ser Glu Leu Glu Lys Gly Leu Ser Lys Lys Gly Val
                50                  55                  60

AAC ATT CCA ATG ATT CCA GGT TGG GTT ATG GAT TTC CCA ACT GGT AAG       1020
Asn Ile Pro Met Ile Pro Gly Trp Val Met Asp Phe Pro Thr Gly Lys
            65                  70                  75
```

FIG. 7A

| | |
|---|---|
| GAA TCC GGT GAT TTC TTG GCC ATT GAT TTG GGT GGT ACC AAC TTG AGA<br>Glu Ser Gly Asp Phe Leu Ala Ile Asp Leu Gly Gly Thr Asn Leu Arg<br>80                          85                          90 | 1068 |
| GTT GTC TTA GTC AAG TTG GGC GGT GAC CGT ACC TTT GAC ACC ACT CAA<br>Val Val Leu Val Lys Leu Gly Gly Asp Arg Thr Phe Asp Thr Thr Gln<br>95                        100                      105 | 1116 |
| TCT AAG TAC AGA TTA CCA GAT GCT ATG AGA ACT ACT CAA AAT CCA GAC<br>Ser Lys Tyr Arg Leu Pro Asp Ala Met Arg Thr Thr Gln Asn Pro Asp<br>110                     115                    120                    125 | 1164 |
| GAA TTG TGG GAA TTT ATT GCC GAC TCT TTG AAA GCT TTT ATT GAT GAG<br>Glu Leu Trp Glu Phe Ile Ala Asp Ser Leu Lys Ala Phe Ile Asp Glu<br>                      130                       135                    140 | 1212 |
| CAA TTC CCA CAA GGT ATC TCT GAG CCA ATT CCA TTG GGT TTC ACC TTT<br>Gln Phe Pro Gln Gly Ile Ser Glu Pro Ile Pro Leu Gly Phe Thr Phe<br>                  145                      150                    155 | 1260 |
| TCT TTC CCA GCT TCT CAA AAC AAA ATC AAT GAA GGT ATC TTG CAA AGA<br>Ser Phe Pro Ala Ser Gln Asn Lys Ile Asn Glu Gly Ile Leu Gln Arg<br>                  160                      165                    170 | 1308 |
| TGG ACT AAA GGT TTT GAT ATT CCA AAC ATT GAA AAC CAC GAT GTT GTT<br>Trp Thr Lys Gly Phe Asp Ile Pro Asn Ile Glu Asn His Asp Val Val<br>    175                        180                      185 | 1356 |
| CCA ATG TTG CAA AAG CAA ATC TCT AAG AGG AAT ATC CCA ATT GAA GTT<br>Pro Met Leu Gln Lys Gln Ile Ser Lys Arg Asn Ile Pro Ile Glu Val<br>190                     195                    200                    205 | 1404 |
| GTT GCT TTG ATA AAC GAC ACT ACC GGT ACT TTG GTT GCT TCT TAC TAC<br>Val Ala Leu Ile Asn Asp Thr Thr Gly Thr Leu Val Ala Ser Tyr Tyr<br>                  210                      215                    220 | 1452 |
| ACT GAC CCA GAA ACT AAG ATG GGT GTT ATC TTC GGT ACT GGT GTC AAT<br>Thr Asp Pro Glu Thr Lys Met Gly Val Ile Phe Gly Thr Gly Val Asn<br>                      225                      230                    235 | 1500 |
| GGT GCT TAC TAC GAT GTT TGT TCC GAT ATC GAA AAG CTA CAA GGA AAA<br>Gly Ala Tyr Tyr Asp Val Cys Ser Asp Ile Glu Lys Leu Gln Gly Lys<br>          240                      245                    250 | 1548 |
| CTA TCT GAT GAC ATT CCA CCA TCT GCT CCA ATG GCC ATC AAC TGT GAA<br>Leu Ser Asp Asp Ile Pro Pro Ser Ala Pro Met Ala Ile Asn Cys Glu<br>    255                        260                    265 | 1596 |
| TAC GGT TCC TTC GAC AAT GAA CAT GTC GTT TTG CCA AGA ACT AAA TAC<br>Tyr Gly Ser Phe Asp Asn Glu His Val Val Leu Pro Arg Thr Lys Tyr<br>270                     275                    280                    285 | 1644 |

FIG. 7B

```
GAT ATC ACC ATT GAT GAA GAA TCT CCA AGA CCA GGC CAA CAA ACC TTT    1692
Asp Ile Thr Ile Asp Glu Glu Ser Pro Arg Pro Gly Gln Gln Thr Phe
            290             295             300

GAA AAA ATG TCT TCT GGT TAC TAC TTA GGT GAA ATT TTG CGT TTG GCC    1740
Glu Lys Met Ser Ser Gly Tyr Tyr Leu Gly Glu Ile Leu Arg Leu Ala
            305             310             315

TTG ATG GAC ATG TAC AAA CAA GGT TTC ATC TTC AAA AAC CAA GAC TTG    1788
Leu Met Asp Met Tyr Lys Gln Gly Phe Ile Phe Lys Asn Gln Asp Leu
            320             325             330

TCT AAG TTC GAC AAG CCT TTC GTC ATG GAC ACT TCT TAC CCA GCC AGA    1836
Ser Lys Phe Asp Lys Pro Phe Val Met Asp Thr Ser Tyr Pro Ala Arg
            335             340             345

ATC GAG GAA GAT CCA TTC GAG AAC CTA GAA GAT ACC GAT GAC TTG TTC    1884
Ile Glu Glu Asp Pro Phe Glu Asn Leu Glu Asp Thr Asp Asp Leu Phe
350             355             360             365

CAA AAT GAG TTC GGT ATC AAC ACT ACT GTT CAA GAA CGT AAA TTG ATC    1932
Gln Asn Glu Phe Gly Ile Asn Thr Thr Val Gln Glu Arg Lys Leu Ile
            370             375             380

AGA CGT TTA TCT GAA TTG ATT GGT GCT AGA GCT GCT AGA TTG TCC GTT    1980
Arg Arg Leu Ser Glu Leu Ile Gly Ala Arg Ala Ala Arg Leu Ser Val
            385             390             395

TGT GGT ATT GCT GCT ATC TGT CAA AAG AGA GGT TAC AAG ACC GGT CAC    2028
Cys Gly Ile Ala Ala Ile Cys Gln Lys Arg Gly Tyr Lys Thr Gly His
            400             405             410

ATC GCT GCA GAC GGT TCC GTT TAC AAC AGA TAC CCA GGT TTC AAA GAA    2076
Ile Ala Ala Asp Gly Ser Val Tyr Asn Arg Tyr Pro Gly Phe Lys Glu
            415             420             425

AAG GCT GCC AAT GCT TTG AAG GAC ATT TAC GGC TGG ACT CAA ACC TCA    2124
Lys Ala Ala Asn Ala Leu Lys Asp Ile Tyr Gly Trp Thr Gln Thr Ser
430             435             440             445

CTA GAC GAC TAC CCA ATC AAG ATT GTT CCT GCT GAA GAT GGT TCC GGT    2172
Leu Asp Asp Tyr Pro Ile Lys Ile Val Pro Ala Glu Asp Gly Ser Gly
            450             455             460

GCT GGT GCC GCT GTT ATT GCT GCT TTG GCC CAA AAA AGA ATT GCT GAA    2220
Ala Gly Ala Ala Val Ile Ala Ala Leu Ala Gln Lys Arg Ile Ala Glu
            465             470             475
```

*FIG. 7C*

```
GGT AAG TCC GTT GGT ATC ATC GGT GCT TAAACTTAAT TTGTAAATTA            2267
Gly Lys Ser Val Gly Ile Ile Gly Ala
        480             485

AGTTTGAACA ACAAGAAGGT GCCCTTTTTT TAATTATGTG AACATGTTTT CTATGATCTT    2327
TTTTTTCTTA CTTTACAACT GTGATATTGT ATAAACTTGT TGAAAATCGA CGGATTATAC    2387
GACGTAATAT TTCGACCTCG AGGGATCTTT GTGAAGGAAC CTTACTTCTG TGGTGTGACA    2447
TAATTGGACA AACTACCTAC AGAGATTTAA AGCTCTAAGG TAAATATAAA ATTTTTAAGT    2507
GTATAATGTG TTAAACTACT GATTCTAATT GTTTGTGTAT TTTAGATTCC AACCTATGGA    2567
ACTGATGAAT GGGAGCAGTG GTGGAATGCC TTTAATGAGG AAAACCTGTT TTGCTCAGAA    2627
GAAATGCCAT CTAGTGATGA TGAGGCTACT GCTGACTCTC AACATTCTAC TCCTCCAAAA    2687
AAGAAGAGAA AGGTAGAAGA CCCCAAGGAC TTTCCTTCAG AATTGCTAAG TTTTTTGAGT    2747
CATGCTGTGT TTAGTAATAG AACTCTTGCT TGCTTTGCTA TTTACACCAC AAAGGAAAAA    2807
GCTGCACTGC TATACAAGAA AATTATGGAA AAATATTCTG TAACCTTTAT AAGTAGGCAT    2867
AACAGTTATA ATCATAACAT ACTGTTTTTT CTTACTCCAC ACAGGCATAG AGTGTCTGCT    2927
ATTAATAACT ATGCTCAAAA ATTGTGTACC TTTAGCTTTT TAATTTGTAA AGGGGTTAAT    2987
AAGGAATATT TGATGTATAG TGCCTTGACT AGAGATCATA ATCAGCCATA CCACATTTGT    3047
AGAGGTTTTA CTTGCTTTAA AAAACCTCCC ACACCTCCCC CTGAACCTGA AACATAAAAT    3107
GAATGCAATT GTTGTTGTTA ACTTGTTTAT TGCAGCTTAT AATGGTTACA AATAAAGCAA    3167
TAGCATCACA AATTTCACAA ATAAAGCATT TTTTTCACTG CATTCTAGTT GTGGTTTGTC    3227
CAAACTCATC AATGTATCTT ATCATGTCTG GATCGCGCCT GATGCGGTAT TTTCTCCTTA    3287
CGCATCTGTG CGGTATTTCA CACCGCATAT G                                   3318
```

*FIG. 7D*

SEQUENCE LISTING

<160> NUMBER OF SEQ ID NOS: 4

<210> SEQ ID NO 1
<211> LENGTH: 3318
<212> TYPE: DNA
<213> ORGANISM: yeast
<220> FEATURE:
<221> NAME/KEY: CDS
<222> LOCATION: (790)..(2247)

<400> SEQUENCE: 1

```
gatcccccaa ccactccaag tggaggctga gaaaggtttt gtagctgggt agagtatgta      60
ctaagagatg gagacagctg gctctgagct ctgaagcaag cacctcttat ggagagttgc     120
tgaccttcag gtgcaaatct aagatactac aggagaatac accatgggct tcagcccagt     180
tgactcccga gtgggctatg ggtttgtgga aggagagata gaagagaagg gacctttctt     240
```

-continued

```
cttgaattct gctttccttc tacctctgag ggtgagctgg ggtctcagct gaggtgagga    300
cacagctatc agtgggaact gtgaaacaac agttcaaggg acaaagttac taggtccccc    360
aacaactgca gcctcctggg gaatgatgtg gaaaaatgct cagccaagga caaagaaggc    420
ctcaccctct ctgagacaat gtccctgct gtgaactggt tcatcaggcc acccaggagc    480
ccctcttaag actctaatta ccctaaggct aagtagaggt gttgttgtcc aatgagcact    540
ttctgcagac ctagcaccag gcaagtgttt ggaaactgca gcttcagccc ctctggccat    600
ctgctgatcc acccttaatg ggacaaacag caaagtccag gggtcagggg ggggtgctt    660 tggactataa agctagtggg gattcagtaa cccccagccc taagtgacca agctattttt    720
tcgctttttc tttgaaaagg ttgtaggaat ataattctcc acacataata agtacgctaa    780 ttaaataaa atg gtt cat tta ggt cca aaa aaa cca caa gcc aga aag ggt    831
          Met Val His Leu Gly Pro Lys Lys Pro Gln Ala Arg Lys Gly
          1               5                  10 tcc atg gcc gat gtg cca aag gaa ttg atg caa caa att gag att ttt    879
Ser Met Ala Asp Val Pro Lys Glu Leu Met Gln Gln Ile Glu Ile Phe
15              20                  25                  30 gaa aaa att ttc act gtt cca act gaa act tta caa gcc gtt acc aag    927
Glu Lys Ile Phe Thr Val Pro Thr Glu Thr Leu Gln Ala Val Thr Lys
            35                  40                  45 cac ttc att tcc gaa ttg gaa aag ggt ttg tcc aag aaa ggt gtt aac    975
His Phe Ile Ser Glu Leu Glu Lys Gly Leu Ser Lys Lys Gly Val Asn
        50                  55                  60 att cca atg att cca ggt tgg gtt atg gat ttc cca act ggt aag gaa    1023
Ile Pro Met Ile Pro Gly Trp Val Met Asp Phe Pro Thr Gly Lys Glu
65              70                  75 tcc ggt gat ttc ttg gcc att gat ttg ggt ggt acc aac ttg aga gtt    1071
Ser Gly Asp Phe Leu Ala Ile Asp Leu Gly Gly Thr Asn Leu Arg Val
    80                  85                  90 gtc tta gtc aag ttg ggc ggt gac cgt acc ttt gac acc act caa tct    1119
Val Leu Val Lys Leu Gly Gly Asp Arg Thr Phe Asp Thr Thr Gln Ser
95              100                 105                 110 aag tac aga tta cca gat gct atg aga act act caa aat cca gac gaa    1167
Lys Tyr Arg Leu Pro Asp Ala Met Arg Thr Thr Gln Asn Pro Asp Glu
            115                 120                 125 ttg tgg gaa ttt att gcc gac tct ttg aaa gct ttt att gat gag caa    1215
Leu Trp Glu Phe Ile Ala Asp Ser Leu Lys Ala Phe Ile Asp Glu Gln
        130                 135                 140 ttc cca caa ggt atc tct gag cca att cca ttg ggt ttc acc ttt tct    1263
Phe Pro Gln Gly Ile Ser Glu Pro Ile Pro Leu Gly Phe Thr Phe Ser
    145                 150                 155 ttc cca gct tct caa aac aaa atc aat gaa ggt atc ttg caa aga tgg    1311
Phe Pro Ala Ser Gln Asn Lys Ile Asn Glu Gly Ile Leu Gln Arg Trp
160                 165                 170 act aaa ggt ttt gat att cca aac att gaa aac cac gat gtt gtt cca    1359
Thr Lys Gly Phe Asp Ile Pro Asn Ile Glu Asn His Asp Val Val Pro
175                 180                 185                 190 atg ttg caa aag caa atc tct aag agg aat atc cca att gaa gtt gtt    1407
Met Leu Gln Lys Gln Ile Ser Lys Arg Asn Ile Pro Ile Glu Val Val
            195                 200                 205 gct ttg ata aac gac act acc ggt act ttg gtt gct tct tac tac act    1455
Ala Leu Ile Asn Asp Thr Thr Gly Thr Leu Val Ala Ser Tyr Tyr Thr
        210                 215                 220 gac cca gaa act aag atg ggt gtt atc ttc ggt act ggt gtc aat ggt    1503
Asp Pro Glu Thr Lys Met Gly Val Ile Phe Gly Thr Gly Val Asn Gly
225                 230                 235
```

-continued

| | |
|---|---|
| gct tac tac gat gtt tgt tcc gat atc gaa aag cta caa gga aaa cta<br>Ala Tyr Tyr Asp Val Cys Ser Asp Ile Glu Lys Leu Gln Gly Lys Leu<br>240                        245                        250 | 1551 |
| tct gat gac att cca cca tct gct cca atg gcc atc aac tgt gaa tac<br>Ser Asp Asp Ile Pro Pro Ser Ala Pro Met Ala Ile Asn Cys Glu Tyr<br>255                        260                        265                      270 | 1599 |
| ggt tcc ttc gac aat gaa cat gtc gtt ttg cca aga act aaa tac gat<br>Gly Ser Phe Asp Asn Glu His Val Val Leu Pro Arg Thr Lys Tyr Asp<br>                     275                        280                        285 | 1647 |
| atc acc att gat gaa gaa tct cca aga cca ggc caa caa acc ttt gaa<br>Ile Thr Ile Asp Glu Glu Ser Pro Arg Pro Gly Gln Gln Thr Phe Glu<br>290                        295                        300 | 1695 |
| aaa atg tct tct ggt tac tac tta ggt gaa att ttg cgt ttg gcc ttg<br>Lys Met Ser Ser Gly Tyr Tyr Leu Gly Glu Ile Leu Arg Leu Ala Leu<br>                 305                        310                        315 | 1743 |
| atg gac atg tac aaa caa ggt ttc atc ttc aaa aac caa gac ttg tct<br>Met Asp Met Tyr Lys Gln Gly Phe Ile Phe Lys Asn Gln Asp Leu Ser<br>320                        325                        330 | 1791 |
| aag ttc gac aag cct ttc gtc atg gac act tct tac cca gcc aga atc<br>Lys Phe Asp Lys Pro Phe Val Met Asp Thr Ser Tyr Pro Ala Arg Ile<br>335                        340                        345                      350 | 1839 |
| gag gaa gat cca ttc gag aac cta gaa gat acc gat gac ttg ttc caa<br>Glu Glu Asp Pro Phe Glu Asn Leu Glu Asp Thr Asp Asp Leu Phe Gln<br>                     355                        360                        365 | 1887 |
| aat gag ttc ggt atc aac act act gtt caa gaa cgt aaa ttg atc aga<br>Asn Glu Phe Gly Ile Asn Thr Thr Val Gln Glu Arg Lys Leu Ile Arg<br>                 370                        375                        380 | 1935 |
| cgt tta tct gaa ttg att ggt gct aga gct gct aga ttg tcc gtt tgt<br>Arg Leu Ser Glu Leu Ile Gly Ala Arg Ala Ala Arg Leu Ser Val Cys<br>385                        390                        395 | 1983 |
| ggt att gct gct atc tgt caa aag aga ggt tac aag acc ggt cac atc<br>Gly Ile Ala Ala Ile Cys Gln Lys Arg Gly Tyr Lys Thr Gly His Ile<br>400                        405                        410 | 2031 |
| gct gca gac ggt tcc gtt tac aac aga tac cca ggt ttc aaa gaa aag<br>Ala Ala Asp Gly Ser Val Tyr Asn Arg Tyr Pro Gly Phe Lys Glu Lys<br>415                        420                        425                      430 | 2079 |
| gct gcc aat gct ttg aag gac att tac ggc tgg act caa acc tca cta<br>Ala Ala Asn Ala Leu Lys Asp Ile Tyr Gly Trp Thr Gln Thr Ser Leu<br>                 435                        440                        445 | 2127 |
| gac gac tac cca atc aag att gtt cct gct gaa gat ggt tcc ggt gct<br>Asp Asp Tyr Pro Ile Lys Ile Val Pro Ala Glu Asp Gly Ser Gly Ala<br>450                        455                        460 | 2175 |
| ggt gcc gct gtt att gct gct ttg gcc caa aaa aga att gct gaa ggt<br>Gly Ala Ala Val Ile Ala Ala Leu Ala Gln Lys Arg Ile Ala Glu Gly<br>465                        470                        475 | 2223 |
| aag tcc gtt ggt atc atc ggt gct taaacttaat ttgtaaatta agtttgaaca<br>Lys Ser Val Gly Ile Ile Gly Ala<br>480                        485 | 2277 |
| acaagaaggt gccctttttt taattatgtg aacatgtttt ctatgatctt ttttttctta | 2337 |
| ctttacaact gtgatattgt ataaacttgt tgaaaatcga cggattatac gacgtaatat | 2397 |
| ttcgacctcg agggatcttt gtgaaggaac cttacttctg tggtgtgaca taattggaca | 2457 |
| aactacctac agagatttaa agctctaagg taaatataaa attttaagt gtataatgtg | 2517 |
| ttaaactact gattctaatt gtttgtgtat tttagattcc aacctatgga actgatgaat | 2577 |
| gggagcagtg gtggaatgcc tttaatgagg aaaacctgtt ttgctcagaa gaatgccat | 2637 |
| ctagtgatga tgaggctact gctgactctc aacattctac tcctccaaaa aagaagagaa | 2697 |
| aggtagaaga ccccaaggac tttccttcag aattgctaag ttttttgagt catgctgtgt | 2757 |

-continued

```
ttagtaatag aactcttgct tgctttgcta tttacaccac aaaggaaaaa gctgcactgc    2817
tatacaagaa aattatggaa aaatattctg taacctttat aagtaggcat aacagttata    2877
atcataacat actgtttttt cttactccac acaggcatag agtgtctgct attaataact    2937
atgctcaaaa attgtgtacc tttagctttt taatttgtaa aggggttaat aaggaatatt    2997
tgatgtatag tgccttgact agagatcata atcagccata ccacatttgt agaggtttta    3057
cttgctttaa aaacctccc acacctcccc ctgaacctga aacataaaat gaatgcaatt     3117
gttgttgtta acttgtttat tgcagcttat aatggttaca aataaagcaa tagcatcaca    3177
aatttcacaa ataaagcatt tttttcactg cattctagtt gtggtttgtc caaactcatc    3237
aatgtatctt atcatgtctg gatcgcgcct gatgcggtat tttctcctta cgcatctgtg    3297
cggtatttca caccgcatat g                                              3318
```

<210> SEQ ID NO 2
<211> LENGTH: 486
<212> TYPE: PRT
<213> ORGANISM: yeast

<400> SEQUENCE: 2

```
Met Val His Leu Gly Pro Lys Lys Pro Gln Ala Arg Lys Gly Ser Met
1               5                   10                  15

Ala Asp Val Pro Lys Glu Leu Met Gln Gln Ile Glu Ile Phe Glu Lys
            20                  25                  30

Ile Phe Thr Val Pro Thr Glu Thr Leu Gln Ala Val Thr Lys His Phe
        35                  40                  45

Ile Ser Glu Leu Glu Lys Gly Leu Ser Lys Lys Gly Val Asn Ile Pro
    50                  55                  60

Met Ile Pro Gly Trp Val Met Asp Phe Pro Thr Gly Lys Glu Ser Gly
65                  70                  75                  80

Asp Phe Leu Ala Ile Asp Leu Gly Gly Thr Asn Leu Arg Val Val Leu
                85                  90                  95

Val Lys Leu Gly Gly Asp Arg Thr Phe Asp Thr Gln Ser Lys Tyr
            100                 105                 110

Arg Leu Pro Asp Ala Met Arg Thr Thr Gln Asn Pro Asp Glu Leu Trp
        115                 120                 125

Glu Phe Ile Ala Asp Ser Leu Lys Ala Phe Ile Asp Glu Gln Phe Pro
    130                 135                 140

Gln Gly Ile Ser Glu Pro Ile Pro Leu Gly Phe Thr Phe Ser Phe Pro
145                 150                 155                 160

Ala Ser Gln Asn Lys Ile Asn Glu Gly Ile Leu Gln Arg Trp Thr Lys
                165                 170                 175

Gly Phe Asp Ile Pro Asn Ile Glu Asn His Asp Val Val Pro Met Leu
            180                 185                 190

Gln Lys Gln Ile Ser Lys Arg Asn Ile Pro Ile Glu Val Val Ala Leu
        195                 200                 205

Ile Asn Asp Thr Thr Gly Thr Leu Val Ala Ser Tyr Tyr Thr Asp Pro
    210                 215                 220

Glu Thr Lys Met Gly Val Ile Phe Gly Thr Gly Val Asn Gly Ala Tyr
225                 230                 235                 240

Tyr Asp Val Cys Ser Asp Ile Glu Lys Leu Gln Gly Lys Leu Ser Asp
                245                 250                 255

Asp Ile Pro Pro Ser Ala Pro Met Ala Ile Asn Cys Glu Tyr Gly Ser
            260                 265                 270
```

```
Phe Asp Asn Glu His Val Val Leu Pro Arg Thr Lys Tyr Asp Ile Thr
        275                 280                 285

Ile Asp Glu Glu Ser Pro Arg Pro Gly Gln Gln Thr Phe Glu Lys Met
    290                 295                 300

Ser Ser Gly Tyr Tyr Leu Gly Glu Ile Leu Arg Leu Ala Leu Met Asp
305                 310                 315                 320

Met Tyr Lys Gln Gly Phe Ile Phe Lys Asn Gln Asp Leu Ser Lys Phe
                325                 330                 335

Asp Lys Pro Phe Val Met Asp Thr Ser Tyr Pro Ala Arg Ile Glu Glu
            340                 345                 350

Asp Pro Phe Glu Asn Leu Glu Asp Thr Asp Asp Leu Phe Gln Asn Glu
            355                 360                 365

Phe Gly Ile Asn Thr Thr Val Gln Glu Arg Lys Leu Ile Arg Arg Leu
    370                 375                 380

Ser Glu Leu Ile Gly Ala Arg Ala Ala Arg Leu Ser Val Cys Gly Ile
385                 390                 395                 400

Ala Ala Ile Cys Gln Lys Arg Gly Tyr Lys Thr Gly His Ile Ala Ala
            405                 410                 415

Asp Gly Ser Val Tyr Asn Arg Tyr Pro Gly Phe Lys Glu Lys Ala Ala
            420                 425                 430

Asn Ala Leu Lys Asp Ile Tyr Gly Trp Thr Gln Thr Ser Leu Asp Asp
            435                 440                 445

Tyr Pro Ile Lys Ile Val Pro Ala Glu Asp Gly Ser Gly Ala Gly Ala
    450                 455                 460

Ala Val Ile Ala Ala Leu Ala Gln Lys Arg Ile Ala Glu Gly Lys Ser
465                 470                 475                 480

Val Gly Ile Ile Gly Ala
                485

<210> SEQ ID NO 3
<211> LENGTH: 24
<212> TYPE: DNA
<213> ORGANISM: Yeast

<400> SEQUENCE: 3
gctctgaagc aagcacctct tatg                                        24

<210> SEQ ID NO 4
<211> LENGTH: 22
<212> TYPE: DNA
<213> ORGANISM: Yeast

<400> SEQUENCE: 4
ggaaatgaag tgcttggtaa cg                                          22
```

PANCREATIC β CELL HEXOKINASE TRANSGENE

BACKGROUND OF THE INVENTION

Diabetes is a disease which effects many Americans. It is a disorder of carbohydrate metabolism characterized by hyperglycemia and glycosuria and resulting from inadequate production or utilization of insulin. The disease takes several different forms and is generally classified into two syndromes: Type I, or insulin-dependent diabetes mellitus (IDDM) and type II, or non-insulin-dependent diabetes mellitus (NIDDM). In Type I the patients secrete little or no insulin. In Type II the individual is able to produce insulin but for whatever reason the individual does not secrete enough insulin to control hyperglycemia. Type II is the most prevalent form of the disease and effects approximately 2–4% of individuals. Current treatment of diabetes Type II (NIDDM) involves constant maintenance of diet and often insulin therapy.

Ordinarily, after insulin is secreted by the β cells of the pancreas it is transported to the cells of the body where it binds to specific insulin receptors. The insulin then acts to promote glucose metabolism in the cell and to inhibit glucose production by the liver.

The basic cause for diabetes is still uncertain but the pathological defect involves failure of the β cells of the pancreas to secrete an adequate amount of insulin. In the absence of sufficient insulin, gluconeogenesis is stimulated, glycolysis is adversely affected and glucose uptake is reduced. All of these factors contribute to diabetic hyperglycemia.

Glucose is the primary regulator of insulin secretion. It is well established that glucose must be metabolized for insulin secretion to ensue. The rate of insulin secretion closely parallels its metabolic rate and inhibitors of glucose metabolism effectively block insulin secretion. In all cells glucose metabolism is initiated by hexokinase-catalyzed phosphorylation. Unique to the pancreatic β cell and the hepatocyte of the liver, this reaction is catalyzed by an unusual hexokinase isoform, hexokinase IV (commonly referred to as glucokinase due to its relative specificity for glucose as a substrate). Hexokinase IV has a $K_m$ for glucose in the physiological range of glucose levels, ≈10 mM. This is almost two orders of magnitude higher than any other mammalian hexokinase. Therefore, in vivo hexokinase IV-catalyzed phosphorylation is proportional to blood glucose levels, whereas phosphorylation by other hexokinases is saturated at physiological glucose levels. Hexokinase IV is also distinct from other hexokinases in that it is not allosterically inhibited by its product, glucose 6-phosphate (G6P). Due to the high $K_m$ of hexokinase IV and the absence of end-product inhibition, glucose phosphorylation in the β cell closely parallels circulating glucose concentrations. It has therefore been proposed that hexokinase IV functions as the glucose receptor or glucose sensor of the pancreatic β cell.

In non-insulin-dependent diabetes mellitus (NIDDM), there is a failure to secrete adequate amounts of insulin despite the fact that pancreatic islets retain significant levels of insulin. (Stefan, Y. et al. (1982) Diabetes 31,694–700.) The secretory deficit appears to be specific for glucose-induced secretion as other secretagogues retain normal efficacy. (Palmer, J. P. et al, (1976) J. Clin. Invest. 58,565–570). The hypothesis that hexokinase IV may serve as the β-cell glucose sensor has taken on great clinical significance recently since it has been demonstrated that a nonsense mutation in only one allele of the hexokinase IV gene predisposes to some types of NIDDM. (Vionnet, N. et al (1992) Nature (London) 356,721–722.) As hexokinase IV is a monomeric enzyme, these results suggest that a simple 50% reduction in hexokinase IV activity due to mutational inactivation of one allele may lead to diabetes.

Thus it can be seen a need exists in the art for further study of the causes of diabetes which may lead to a potential cure, as well as a test of the hypothesis that hexokinase IV may serve as the glucose β-cell sensor. It is an object of the present invention to provide a transgene which expresses a 2-fold increase in hexokinase activity for study of the role of hexokinase in insulin secretion and diabetes.

It is another object of the present invention to provide a method of decreasing diabetes by stimulating hexokinase activity and thereby increase insulin secretion for Type II diabetic patients.

It is yet another object of the present invention to provide an animal model for study of diabetes or other glucose regulatory mechanisms in which the animal model experiences a 2-fold increase in hexokinase activity which is specific to the β cell.

SUMMARY OF THE INVENTION

The present invention relates to construction of a transgene comprising the yeast hexokinase B gene (yeast hexokinase B like hexokinase IV is not allosterically inhibited by intracellular levels of G6P) operatively linked to an insulin promoter. The transgene, when inserted into mice resulted in a 2-fold increase in hexokinase activity. The increase was found to significantly augment glucose stimulated insulin secretion of isolated pancreatic islets, to increase serum insulin levels in vivo, and to lower blood glucose levels of transgenic animals by 20–50% below control levels.

The transgene of the present invention may be introduced into an animal model for study of the disease, or may be used for direct manipulation of pancreatic β cells for possible treatment for diabetes.

DESCRIPTION OF THE DRAWINGS

FIG. 1 is a schematic of the transgene constructed to elevate hexokinase levels in pancreatic β cells of transgenic mice. The /box designated as RIP indicates the first of 709 base pairs of the rat insulin II gene. The open box designated as hexokinase indicates the complete coding sequence of the yeast hexokinase β gene. The hatched region indicates sequences from the SV40 virus to provide polyadenylation sequences. The polyadenylation and initiation codon are indicated by AATAAA and ATG respectively.

Vertical lines are the standard error of the mean. Indicated tissues are H, heart; K, kidney; B, brain; L, liver; I, islets.

FIGS. 7A–7D is the genetic sequence which was introduced into mice to create the transgenic animals of the invention. Nucleotides 1–709 are from the rat insulin promoter and gene (1–695) are the promoter and 696–709 are untranslated sequences which were part of the mRNA. Nucleotides 710–714 are from a Hind III linker, and nucleotides 715 to 2395 are from the yeast hexokinase B gene. (Nucleotides 2396–3261 are SV–40 sequences from a commercial plasmid MSG (Pharmacia); and nucleotides 3262–3318 are from plasmid PVC18 which are without function.)

DETAILED DESCRIPTION OF THE INVENTION

The present invention relates to an animal model of hypoglycemia for use in study and a genetic construct which may be transformed to animals to reduce the affects of diabetes. Such model could be useful for study of the role of hexokinase in diabetes, and regulation of the glucose set point of individuals, as well as a potential treatment for direct manipulation of pancreatic β cells for possible treatment of diabetes. Other attempts to try to increase hexokinase activity have proved largely unsuccessful to date. Applicant's invention comprises a workable model for elevation of hexokinase levels by use of a hexokinase gene (the yeast hexokinase IV gene) preferably in combination with an operable promoter.

In one embodiment of the invention, the exogenous sequences encoding hexokinase IV may be introduced to a non-human vertebrae animal model (preferably a mammal such as a rodent e.g. a mouse) to create an animal model which over expresses hexokinase. The resulting transgenic mouse may be used to study the effects of hexokinase on overall glucose and insulin regulation in the individual and may be crossbred with a diabetic mouse to determine effects of hexokinase over expression on diabetic (NIDDM) individuals. Generally the transgenic sequence is introduced into the animal, or an ancestor of the animal, at an embryonic stage (preferably one cell or fertilized oocyte, stage, and generally not later than about the 8-cell stage). The transgene preferably is substantially homologous with hexokinase IV and in a preferred embodiment is linked to an operable promoter for controlled expression of the hexokinase.

There are several means by which transgenic animals can be made known to those of skill in the art. One method involves use of transfecting retrovirus or adenovirus containing the transgenic sequence. Another method involves directly injecting the transgene into the embryo. Another method employs the embryonic stem cell methodology known to workers in this field.

Introduction of the recombinant gene at the fertilized oocyte stage insures that the gene sequence will be present in half of the germ cells and all of the somatic cells of the transgenic (founder) animal. The presence of the recombinant gene sequence in the germ cells of the transgenic founder animal in turn means that approximately half of the founder animals descendants will carry the activated hexokinase over expression sequence in half of their germ cells and all of their somatic cells. Introduction of the recombinant gene sequence at a later embryonic stage might result in the gene's absence from some somatic cells of the founder animal, but the descendants of such animal that inherit the gene will carry the recombinant gene in half of the germ and all of the somatic cells.

The animals of the invention can be used as models as potential use for the treatment of diabetes as well as the role of hexokinase in the overall glucose insulin regulation of the animal. Further the animals of the invention can be used as a source for cells for cell culture, to study the in vitro effects of hexokinase or for a source of islets or beta cells for transplantation.

The transgenic segment also optionally includes a promoter which is very active in pancreatic β cells such as rat insulin promoter. Other useful promoters include the CMV promotor from cytomegalovirus or the RSV LTR promoter from Rous saroma virus. These promoters should have the effect of inducing expression of the hexokinase in the pancreatic B cell.

A transgene designated Inshex was constructed consisting of 709 bp of the rat insulin II gene including the promoter linked to the intronless yeast hexokinase B gene as disclosed in Stachelek, et al (1986) Nucleic Acids Res. 14:945–963 and polyadenylylation sequences derived from the simian virus 40 early region. The yeast hexokinase gene was chosen because yeast hexokinase B, like hexokinase IV, is free from allosteric inhibition by G-6-P and catalyzes the same reaction as hexokinase IV. Additionally yeast hexokinase B has a higher affinity for glucose than hexokinase IV and, therefore, should produce a more obvious effect on β-cell function. It should be noted for purposes of the invention that several different transgenic sequences may be created for introduction into the mice of the invention as known by those of skill in the art and at its simplest level, the invention embodies a transgene which may be inserted into expression systems comprising a sequence which encodes upon expression, hexokinase, and which is linked to an operable promoter which is active in the cell.

EXAMPLES

Construction of the Inshex Gene and Production of Transgenic Mice

A transgenic sequence was constructed, (named Inshex) according to the present invention. The Inshex gene comprised a yeast hexokinase B gene linked to rat insulin II promoter. The fragment of the rat insulin II promoter utilized to direct β-cell-specific expression has been described. Hanahan, D. (1985) Nature (London) 315, 115–122. This promoter fragment contains 695 base pairs (bp) of sequence 5' to the insulin transcription initiation site and 14 bp 3' to the insulin transcription initiation site. A HindIII linker was inserted 3' to the initiation site as described in Epstein, P. N., (1989) Cell 58, 1063–1073. The yeast hexokinase B gene (provided by W. Konigsberg, Yale University, New Haven, Conn.), contained in a 1681-bp Ssp I fragment that included the entire coding sequence, was inserted behind the insulin promoter by blunt-end ligation using the HindIII linker mentioned above. An 866-bp Sal I-BamHI fragment of simian virus 40 (derived from the plasmid PMSG; Pharmacia) containing a simian virus 40 early region splice and polyadenylylation site was inserted behind the hexokinase B gene. For production of transgenic mice, most plasmid sequences were removed from the gene by BamHI/Nde I digestion, and the resultant 3316-bp fragment was purified as described in the Cell publication. The sequence is disclosed as SEQ ID NO.:1 and is listed in FIG. 7.

Transgenic mice were generated by microinjection of the DNA construct into single-cell embryos by standard techniques. Gordon et al (1983) Method Enzymol. 101, 411–433. Embryos were isolated from superovulated 4- to 6-week-old FVB/N females. Microinjections of purified DNA at 2 μg/ml in 10 mM Tris-HCl/0.1 mM EDTA, pH 7.6, were into one pronucleus for each embryo, 12–14 hours after fertilization. Embryos that survived microinjection were implanted into pseudopregnant females and allowed to develop to term. Founder mice were crossed with ICR mates and transgenic lines were maintained on an ICR background.

DNA and RNA Analyses

Founder mice were identified on Southern blots prepared with 10 μg of tail DNA digested with EcoRI. Blots were hybridized to a 1200-bp HindIII-Xho I fragment of the Inshex gene radiolabeled with $^{32}$P by random priming. Routine identification of transgenic mice was made by PCR analysis with oligonucleotides identical to the rat insulin II promoter between positions 88 and 113 (GCTCTGAAGCAAGCACCTCTTATG) SEQ ID NO:3 and complementary to the yeast hexokinase coding sequence 125 bp 3' to the translation start site (GGAAATGAAGTGCTTGGTAACG) SEQ ID NO:4.

Expression of yeast hexokinase RNA was determined by S1 nuclease protection analysis of poly(A)$^+$ pancreatic RNA. Poly(A)$^+$ RNA was prepared on oligo(dT) columns from pancreatic RNA isolated by the guanidinium thiocyanate method. An RNA probe was prepared from an 1125-bp fragment of the Inshex gene, from position 75 in the insulin promoter to a HindIII site in the hexokinase coding sequence, 505 bp 3' of the expected transcription initiation site of the insulin promoter.

This fragment was inserted into plasmid pSP64, cut with EcoRI in the insulin promoter and in the pSP64 polylinker and radiolabeled with SP6 polymerase and [$^{32}$P]CTP. The radiolabeled RNA probe was hybridized to pancreatic poly (A)$^+$ RNA in 80% (vol/vol) formamide at 50° C. and digested with 1000 units of S1 nuclease at 37° C. Protected products were identified by PAGE and autoradiography. $^{32}$P-end-labeled Hae III digests of plasmid φ-174 served served as molecular size standards.

Islet Isolation

Transgenic and normal islets were isolated in parallel from 1- to 2-week old litters. Genotype was determined by PCR analysis as described above. Islets were released from pancreatic acinar tissue by digestion with collagenase P (Boehringer). After two washes in Hanks' balanced salt solution, islets were purified by centrifugation on Percoll (Pharmacia) gradients. Brunstedt, J. (1980) Diabete Metab. 6, 87–89. Islets were then further purified by picking under a dissection microscope. In most instances, islets were cultured overnight in RPMI 1640 medium (GIBCO) containing 10% (vol/vol) fetal calf serum, 5 mM glucose, and 10 mM Hepes (pH 7.4). In these experiments overnight cultured and freshly isolated islets yielded equivalent results.

Islet Assays

Measurement of hexokinase activity was performed by the radiometric procedure of Bedoya et al (1985) Anal. Biochem. 144, 504–513. In brief, batches of 25–50 islets were homogenized in 100 μl of extraction buffer [30 mM Hepes, pH 7.6/130 mM KCl/4 mM MgCl$_2$/14 mM 2-mercaptoethanol/0.2% (wt/vol) bovine serum albumin] and then centrifuged at 60,000×g for 30 minutes and 4° C. Pellets were used for measurement of DNA content. Aliquots (10 μl) of the extract were assayed for hexokinase activity in incubation buffer [50 mM Hepes, pH 7.6/120 mM KCl/8 mM MgCl$_2$/14 mM 2-mercaptoethanol/5 mM ATP/0.1% bovine serum albumin/3 μCi of D-[2-$^3$H(N)glucose/3 mM G6P]. Assays were performed for 60 minutes at 30° C. After the initial incubation, the reaction products were quantitated by measuring the release of $^3$H$_2$O from [$^3$H]G6P by the action of phosphoglucose isomerase (Boehringer). Determinations of hexokinase activity in other tissues were performed by the same procedure.

Insulin secretion was assayed by consecutive static assays of isolated islets in increasing concentrations of glucose (3–15 mM) or ketoisocaproic acid (KIC, 1–9 mM). Assays were performed in modified Krebs-Ringer bicarbonate buffer (KRB =133 mM NaCl/5 mM NaHCO$_3$/5 mM KCl/1.2 mM MgSO$_4$/1.2 mM KH$_2$PO$_4$/2.5 mM CaCl$_2$/15 mM Hepes, pH 7.4/0.1% bovine serum albumin. Briefly, batches of 10–20 islets were picked into tubes containing KRB for a,30-minute preincubation at 37° C. and then the medium was replaced with 0.4 ml of KRB containing the lowest concentration of glucose or KIC to be tested. After 30 minutes at 37° C., the medium was removed for radioimmunoassay of insulin and the incubation medium was replaced with the next higher concentration of secretagogue. After the last incubation, islets were extracted with acidifed ethanol for measurement of islet insulin content. Perifusion assays were performed as described in the method of Atwater et al (1981) J. Physiol. (London) 314, 195–212 on freshly microdissected islets from 3- to 4-month-old transgenic and control mice.

Measurement of Glucose and Insulin

Determinations of insulin levels in serum samples and secretion assays were made by double-antibody RIA using a coated-tube insulin RIA kit (Diagnostic Products, Los Angeles) and rat insulin standards (Novo Biolabs, Danbury, Conn.). Blood samples sufficient for RIA were obtained by decapitation. Serum samples were prepared by centrifugation after incubating blood samples overnight at 4° C. Glucose assays were performed on whole blood with the One Touch blood glucose monitor (Lifescan, Mountain View, Calif.).

Figure 1:
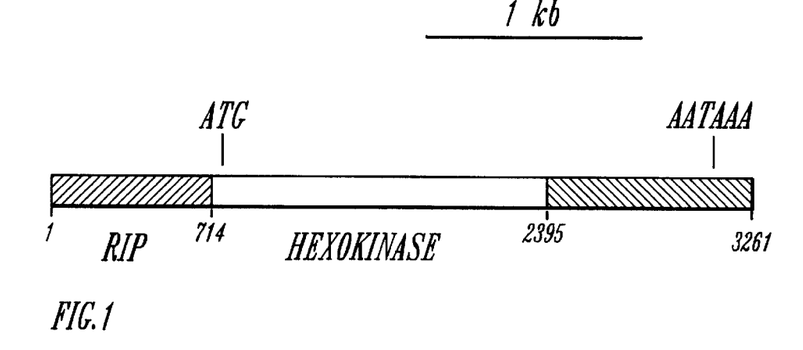

Four founder lines were produced initially that carried one or more copies of the Inshex gene. To determine whether the transgene was expressed pancreatic RNA was isolated from members of each line and subjected to an S1 nuclease protection assay. As shown in FIG. 1A only mice of trangenic line 5032 produced significant levels of RNA complimentary to an antisense yeast hexokinase RNA probe.

An S1 nuclease protection assay of pancreatic RNA indicated that the Inshex gene was transcribed in line 5032. S1 protection assays were performed on pancreatic RNA by using a 32P-labeled RNA probe derived from the Inshex gene. Arrow, predicted position for a 505-nucleotide RNA probe fragment protected by a properly initiated transcript from the Inshex transgene. Sources of pancreatic RNA are as follows: Lanes, 1, control mice; 2, line 5032 mice; 3, line 5039 mice; 4, line 5040 mice; 5, line 5041 mice.

Two additional transgenic lines were made but these also failed to express the transgene. Lack of expression in 5 of 6 transgenic lines may have been due to the absence of introns in the yeast hexokinase gene. Palmiter et al (1991) Proc. Natl. Acad. Sci. USA 88, 478–482.

Figure 2:
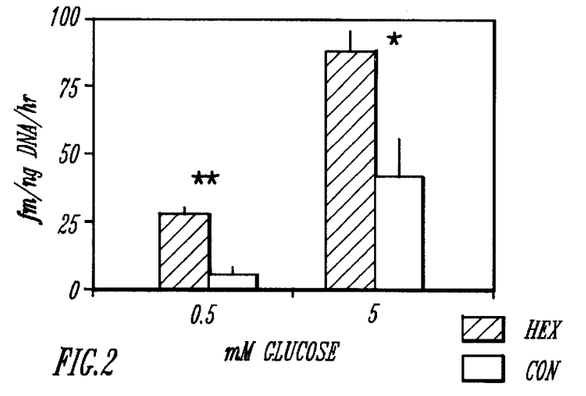
FIG. 2 is a bar graph depicting increased hexokinase activity in the islets of transgenic mice as compared to islets isolated from their non-transgenic siblings. Hexokinase activity was determined from homogenates of islets isolated from transgenic mice (HEX) and their non-transgenic siblings (CON). Assays were performed at the indicated glucose concentrations in the presence of 3 μM glucose 6-phosphate. Islets were isolated and assayed as described in the materials and methods. Different from control **P<0.025, *P<0.05.
Figure 3:
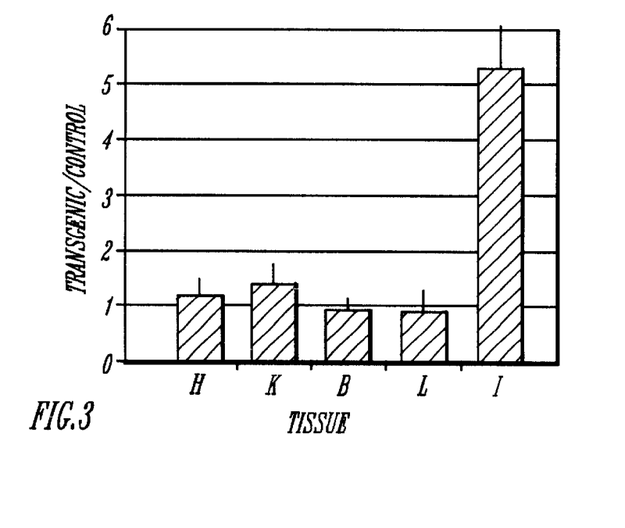
FIG. 3 is a graph depicting the ratio of transgenic to control levels of hexokinase activity in homogenates of various tissues obtained from transgenic and control mice. Four or more assays were performed for each tissue at 0.5 μM glucose in the presence of 3 μM glucose 6-phosphate.

To determine whether production of yeast hexokinase mRNA resulted in elevated enzyme levels, pancreatic islets were isolated from transgenic and non-transgenic siblings of line 5032 and assayed for hexokinase activity. Bedoya, F. J. et al (1985) Anal. Biochem. 144, 504–513. Results are shown in FIG. 2. Transgenic high affinity hexokinase activity was increased 5-fold over normal when measured at 0.5 mM glucose. At 5 mM glucose, selected because it is in the physiological range of glucose concentration, hexokinase activity was increased 2-fold. This moderate increase would be sufficient to affect β-cell function in vivo, if secretion is directly regulated by the rate of glucose phosphorylation. These assays were performed in the presence of 3 mM G6P since G6P is a potent endogenous inhibitor of all mammalian hexokinases except hexokinase IV: in the β cell, intracellular G6P inhibits the endogenous high affinity hexokinase by <90%. Trus, M. C. et al (1981) Diabetes 30, 911–922. To confirm tissue specificity of expression in the pancreatic β cells, hexokinase assays were also performed on brain, liver, kidney and heart from transgenic and non-transgenic mice and the results are shown in FIG. 3. Despite the fact that these assays were performed under conditions of maximal sensitivity for yeast hexokinase (0.5 mM glucose/3 mM G6P), no significant increase in enzyme activity was apparent in these tissues.

Insulin Secretion Increases in in Vitro Isolated Islets

Figure 4:
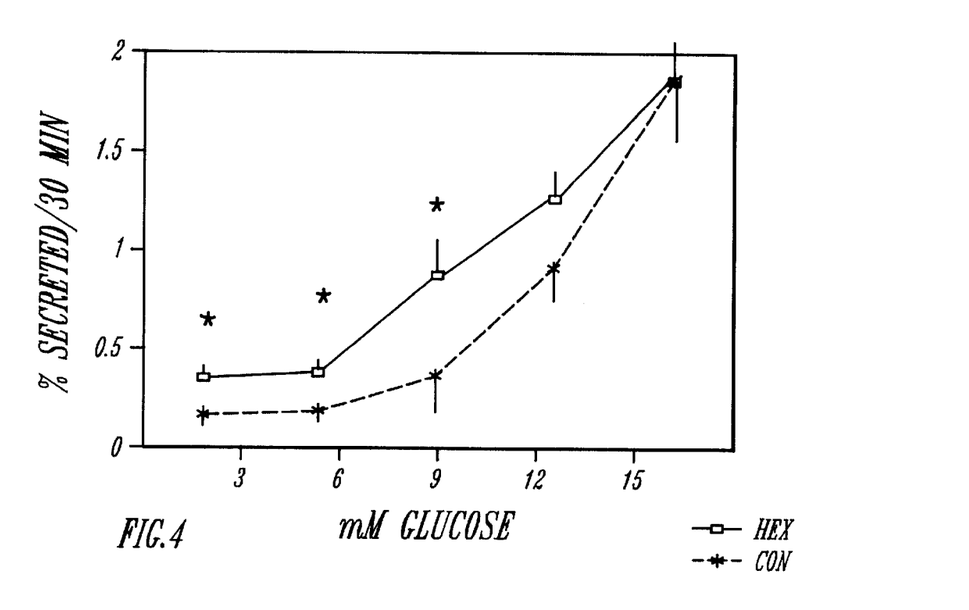
FIG. 4 is a graph depicting glucose stimulated insulin secretion increased in transgenic islets. Transgenic (HEX) and control (CON) islets were isolated in parallel and assayed by consecutive thirty minute incubations at the indicated concentration of glucose. After the last incubation islets were extracted to determine insulin content. Essentially the same results have been obtained in multiple perfusion assays of microdisected islets (data not shown). *different from control P<0.025.

The most direct measurements of β-cell glucose sensitivity can be made in isolated pancreatic islets. Islets were isolated from transgenic mice of line 5032 and their non-transgenic littermates. Insulin secretion was measured by incubating islets successively in increasing concentrations of glucose (FIG. 4). Since yeast hexokinase B has a high affinity for glucose, the greatest effect of this transgene would be at relatively low concentrations of glucose, as was found. At the lower concentrations of glucose tested, 3–9 mM, transgenic secretion rates were ≈2-fold higher than normal (P <0.025). At 15 mM glucose, transgenic and normal secretion rates were essentially the same. If this enhanced secretion to glucose was a direct effect of the enzymatic activity of yeast hexokinase then the secretory response to secretagogues that are not hexokinase substrates should not be affected. KIC was chosen for this test since KIC, like glucose, is a fuel secretagogue dependent on metabolism to induce secretion. However, unlike glucose, KIC is not a substrate for hexokinase; therefore the transgenic hexokinase should not augment KIC-induced secretion. At no concentration of KIC did the transgenic islets demonstrate increased secretion relative to normal islets. These results demonstrate that the enhanced secretion response of transgenic islets was specific to substrates of the transgene and a direct effect of elevated hexokinase activity.

Yeast Hexokinase Responses in Vivo

Figure 5:
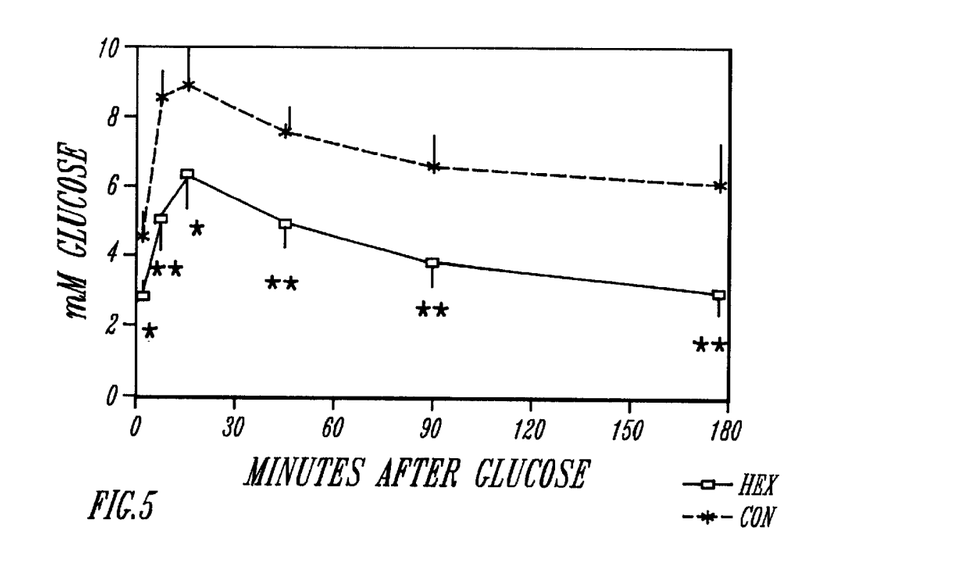
FIG. 5 is a graph depicting lower blood glucose levels of transgenic mice which express hexokinase than control mice. Transgenic mice (HEX) and their non-transgenic siblings (CON) were fasted overnight and then administered in IP injection of 1 mg glucose per gram of body weight. Blood samples were taken at the indicated times from the tail. Blood glucose was determined from a Life Scan glucometer. N=9 or 10 per point. Different from control; *P<0.01, **P<0.001.

The 2-fold elevation of islet hexokinase activity measured at physiological glucose concentrations and the enhancement of glucose-stimulated insulin secretion in isolated islets leads to the conclusion that alterations in β-cell function might be reflected in altered glucose homeostasis of the whole animal. Random blood glucose assays indicated that glucose levels were reduced in line 5032, which expressed the hexokinase transgene and that blood glucose levels were normal in the five nonexpressing lines of transgenic mice. To analyze the reduction in glucose levels of line 5032 systematically, intraperitoneal glucose tolerance tests were performed on overnight-fasted transgenic mice and their nontransgenic siblings (age, 20–30 days). These results, shown in FIG. 5 confirmed that relative to their normal siblings transgenic mice of line 5032 had significantly lower fasted glucose levels, and their peak glucose levels after i.p. administration of glucose were also much lower. In addition, within 180 minutes of glucose administration, transgenic blood glucose values returned to near their original low fasted level. These results indicate that the level of β-cell hexokinase activity controls whole-animal glucose homeostasis. Thus the transgene of the present invention produces a permanent reduction of blood glucose values.

Figure 6:
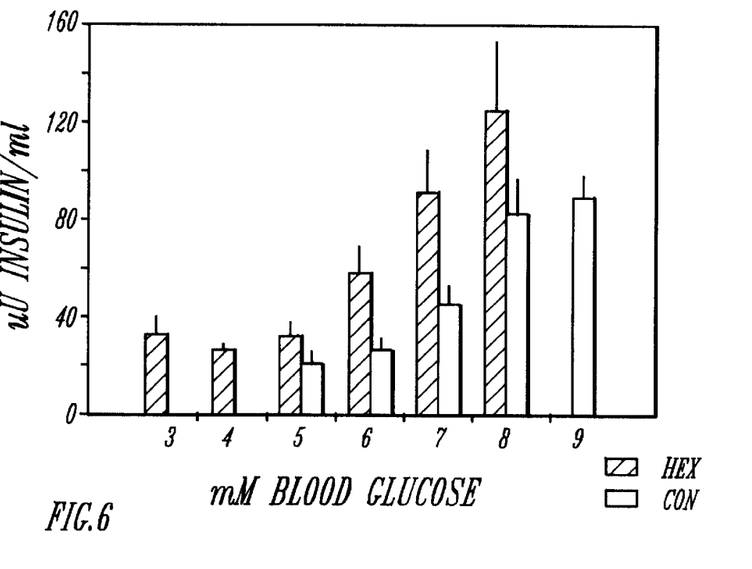
FIG. 6 is a bar graph depicting serum insulin levels relative to blood glucose level for transgenic and control mice. 40–60 day old transgenic (HEX) or normal (CON) mice were free-fed or fasted for 4 to 6 hours. Blood samples were obtained on sacrifice for determination of blood glucose and serum insulin. Samples were grouped on the basis of blood glucose level. At least three determinations were obtained for each point. No control mice had blood glucose levels below 5 mM and no transgenic mice had blood glucose above 8 mM Vertical bars indicate the standard error of the mean.
Figure 7D:
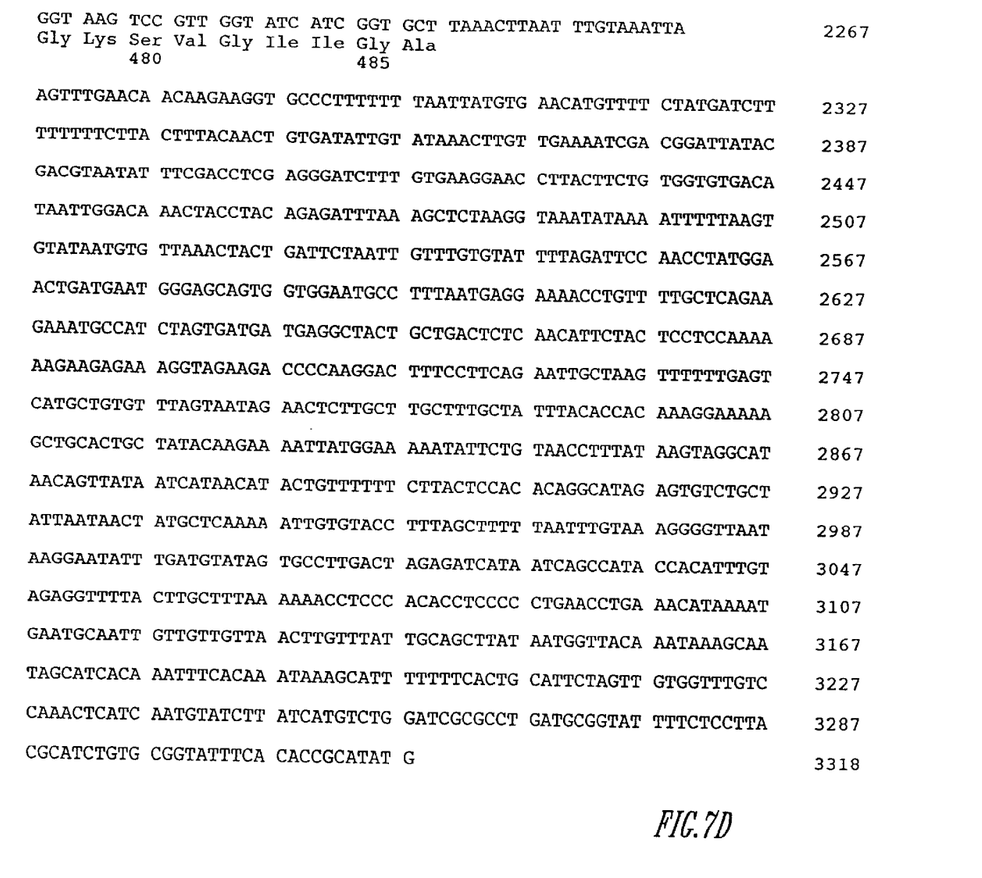

To determine in vivo glucose levels and whether they were a function of enhanced insulin secretion, age-matched transgenic and nontransgenic mice were sacrificed to obtain samples adequate for measurement of serum insulin levels. Prior to sacrifice mice were either free-fed or fasted for 5 hours so that insulin levels could be determined over a broad range of glucose values. Serum insulin and blood glucose levels were determined from the same sample. As shown in FIG. 6, the relationship between blood glucose and serum insulin was markedly shifted by the transgene. Insulin levels in transgenic mice were higher at all glucose values (no control values are shown for 3 and 4 mM glucose since no control mice had glucose levels <5 mM; no transgenic mice had glucose values >8 mM). In addition, the rise in serum insulin levels of hexokinase mice was steeper with increasing blood glucose levels than was seen in control mice. The elevation of serum insulin could not have been due to increased levels of pancreatic insulin, as observed in some transgene-induced β-cell tumors, Hanahan, D. (1985) Nature (London) 315, 115–122, since several assays of total pancreatic insulin content indicated an ≈50% reduction in pancreatic insulin content of hexokinase transgenic mice in both neonates and adults (data not shown). The elevated serum insulin values of transgenic mice over a broad range of glucose values demonstrate in vivo that increased hexokinase activity enhanced insulin secretion and confirmed the altered whole animal glucose homeostasis is a function of enhanced insulin secretion rather than a nutritional or peripheral metabolic effect.

Inshex Transgenic Mice Tested in a Diabetes Model

To determine whether increasing β-cell glucose phosphorylation could be beneficial in diabetes, hexokinase transgenic mice from line 5032 were bred to a diabetic transgenic line. The diabetic line selected was the line OVE26 which overexpresses calmodulin in pancreatic β cells. OVE26 transgenic mice develop diabetes due to an insulin secretory defect and a depletion of pancreatic insulin. Four litters from these crosses were assayed for blood glucose at 24 days of age, which is after the onset of diabetes but before complete destruction of the β-cell population. The results are seen in Table 1 (Genotypes were determined by PCR analysis).

TABLE I

REDUCTION OF DIABETIC GLUCOSE LEVELS
BY THE YEAST HEXOKINASE TRANSGENE

| GENOTYPE | CaM-/Hex+ (5) | CaM-/Hex- (10) | CaM+/Hex+ (10) | Cam+/Hex- (6) |
|---|---|---|---|---|
| Glucose mM | 4.6 ± 0.5 | 8.0 ± 0.3 | 11.6 ± 0.7* | 13.9 ± 0.7 |

N values (in parenthesis) indicate the number of separate mice of each genotype assayed.
*CaM+/Hex+ blood glucose values are less than CaM+/Hex- glucose values, $p < 0.025$ and CaM+/Hex+ glucose values are greater than CaM-/Hex- glucose values (normal littermates) $p < 0.01$.

Hexokinase transgenes significantly reduced diabetic blood glucose levels produced by the calmodulin transgene. Blood glucose values of CaM$^+$/Hex$^+$ mice (transgenic for calmodulin and yeast hexokinase; 11.6 ±0.7 mM glucose; n =10) were 2.3 mM lower than glucose levels of CaM$^+$/Hex$^-$ mice (transgenic for calmodulin only; 13.9 ±0.7; n=6) ($P < 0.025$).

This hexokinase reduction corresponds to approximately 40% of the difference between blood glucose levels of CaM$^+$/Hex$^-$ mice and normal mice (CaM$^-$/Hex$^-$; 8.0 ±0.3; N =10($P<0.01$). Measurements of pancreatic insulin content from several of these mice indicated that the hexokinase transgene exacerbated the calmodulin/induced depletion of pancreatic insulin (data not shown). Apparently the hexokinase activity did not directly reverse the defect produced by calmodulin, however secretion was enhanced despite the defect. Tests on older individuals have revealed that this effect in the calmodulin-induced diabetes model may be transient, as mice who at 21–26 days of age were shown to have the positive benefits of the hexokinase stimulated insulin secretion were later shown by 33–40 days that the benefits were no longer present. However, the blood glucose values of normal mice or mice transgenic for hexokinase alone during the same time period remained constant. Additionally, mice with the hexokinase transgene were found to have lower blood glucose values and higher serum insulin levels than normal mice.

TABLE II

PHENOTYPIC COMPARISON OF NORMAL MICE
AND MICE HETEROZYNGOUS AND HOMOZYGOUS
FOR THE HEXOKINASE TRANSGENE

| GENO-TYPE | uU INSU-LIN/mg PAN-CREAS day 0 | uU INSU-LIN/mg PAN-CREAS day 60–73 | BLOOD GLU-COSE (mg/dl) day 59–70 | SERUM INSULIN (uU/ml) day 59–70 | PER-CENT GLYCO-SYLATED HEMO-GLOBIN |
|---|---|---|---|---|---|
| NORMAL | 15300 ± 3000(4) | 5100 ± 500(10) | 168 ± 8(9) | 27 ± (9) | 3.87 ± 0.18(7) |
| HEXO-KINASE HETERO-ZYGOUS | 18600 ± 2000(11) | 3000 ± 800(4)* | 119 ± 5(5)** | 41 ± 4(5)* | ND |
| HEXO-KINASE HOMO-ZYGOUS | 9500 ± 900(4)# | 2000 ± 200(6)** | 125 ± 7(9)** | 39 ± 4(9)* | 2.99 ± 0.08(8)* |

Values show the mean and the standard error of the mean for each parameter. Values in parentheses indicate the number of animals tested. Day 0 mice are between 0 and 24 hours old. Blood glucose and serum insulin values were obtained from avertin anesthetized mice. Other procedures are described in Materials and Methods. (ND) not determined.
*different from normal by student's t-test, $p < 0.25$
**different from normal by student's t-test, $p < 0.001$
difference from heterozygous student's t-test, $p < 0.05$ This is the first report of a transgene which enhances β-cell function by positively effecting glucose homeostasis. Thus it can be seen that the invention accomplishes at least all of its objectives.

What is claimed is:

1. A transgenic mouse whose germ cells and somatic cells comprise a gene construct comprising a rat insulin II promoter operably linked to a yeast hexokinase gene, wherein said gene construct is integrated into the genome of the transgenic mouse, wherein said hexokinase gene is expressed in the pancreatic beta cells of said transgenic mouse, and wherein expression of said hexokinase gene results in increased insulin and glucose levels in the blood of the transgenic mouse, compared with the insulin and glucose levels in the blood of a mouse that does not express a yeast hexokinase gene in its beta cells.

2. The transgenic mouse of claim 1, wherein said gene construct comprises the sequence of SEQ ID NO 1.

* * * * *